United States Patent [19]

Duffy

[11] Patent Number: 4,844,086

[45] Date of Patent: Jul. 4, 1989

[54] CROSS CORRELATION ANALYSIS IN BRAIN ELECTRICAL ACTIVITY MAPPING

[75] Inventor: Frank H. Duffy, Brighton, Mass.

[73] Assignee: The Children's Medical Center Corporation, Boston, Mass.

[21] Appl. No.: 37,982

[22] Filed: Apr. 13, 1987

[51] Int. Cl.[4] ............................................... A61B 5/04
[52] U.S. Cl. ................................................... 128/731
[58] Field of Search ............................... 128/731–732; 364/413–415

[56] References Cited

U.S. PATENT DOCUMENTS 3,696,808  10/1972  Roy et al. ............................ 128/731
4,408,616  10/1983  Duffy et al. ......................... 128/731

OTHER PUBLICATIONS

Duffy et al., "Brain Electrical Activity Mapping (BEAM): A Method for Extending the Clinical Utility of EEG and Evoked Potential Data" Ann. Neurol., 5:309–321 (1979).

Duffy et al., "Significance Probability Mapping: An Aid in the Topographic Analysis of Brain Electrical Activity", Electroencephalography and Clinical Neurophysiology, 51:455–462 (1981).

Duffy et al., "Topographical Display of Evoked Potentials: Clinical Applications of Brain Electrical Activity Mapping (BEAM)", Anals New York Academy of Sciences, 388:183–196 (1982).

Duffy et al., "Tumor Detection from Topographic Maps of Long Latentcy Evoked Potentials: Spatial Trajectory Analysis and Cross Correlation Analyses", unpublished paper.

Primary Examiner—Francis J. Jaworski

[57] ABSTRACT

A diagnostic method is disclosed wherein brain evoked potential (EP) data from a plurality of electrode sites on the patient's head is gathered and compared with a comparable EP for normal patients by forming (1) the cross-correlation between the patient's EP and the normal EP, (2) the maximum cross-correlation for any time shift in a selected period or $C_{max}$, and (3) the time shift $T_{max}$ at which the maximum correlation occurs. Selected one of these values for particular evoked potentials are used to compute diagnostic feature values, and a plurality of diagnostic feature values are used to achieve a diagnosis of brain pathology.

13 Claims, 4 Drawing Sheets

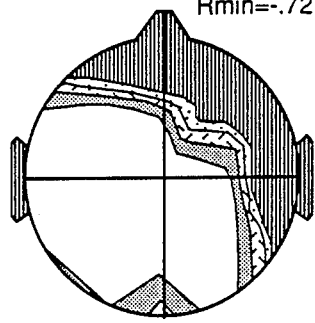
FIG 2A
XC at t=0    Rmax=+.80
             Rmin=-.72
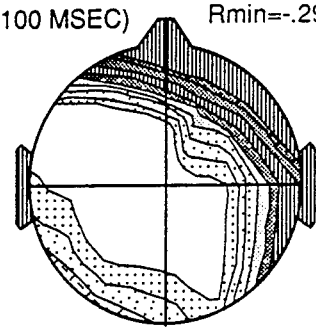
FIG 2B
MAX LAGGED    Rmax=+.92
XC (100 MSEC) Rmin=-.29
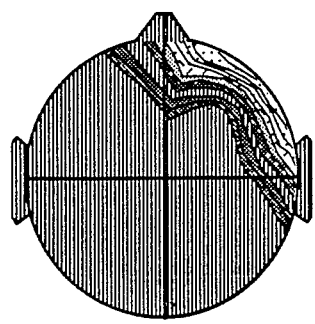
FIG 2C
TIME TO MAX XC   Tmax=96 msec
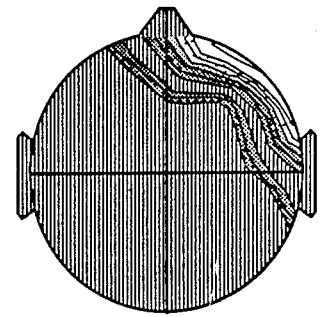
FIG 2D
1-MAX LAGGED XC
FIG 2
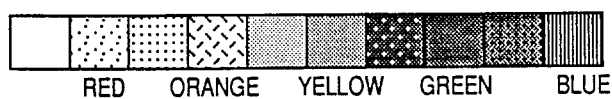
RED   ORANGE   YELLOW   GREEN   BLUE

FIG 3A
AER 280-356 Msec    Zm=3.31
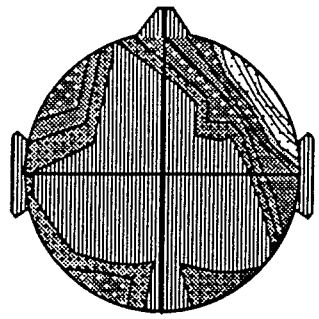
FIG 3
CROSS
CORRELATIONAL
ANALYSIS
(CCA)
FIG 3B
XC at t=0    Rmin=-.02
Rmax=+.80
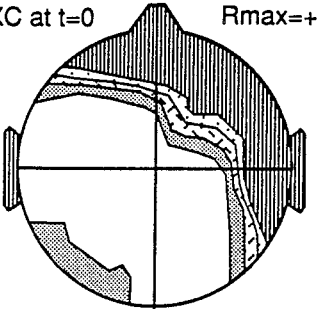
FIG 3C
Max XC    Rmax=+.89
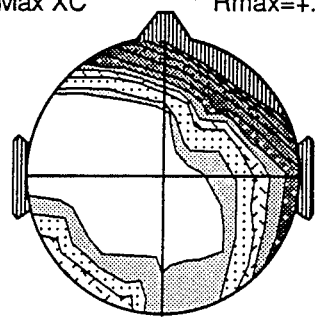
FIG 3D
Time to max XC    Tmax=98 Msec
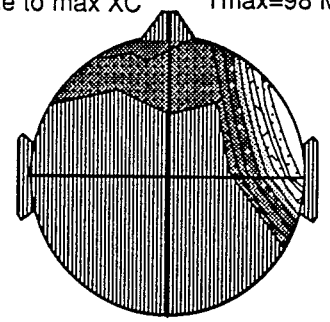
FIG 3E
(1-Rmax) for max XC
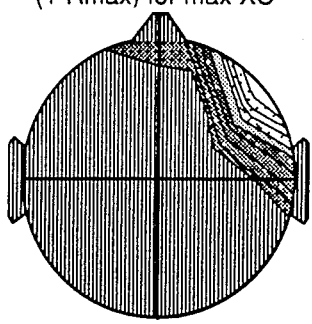
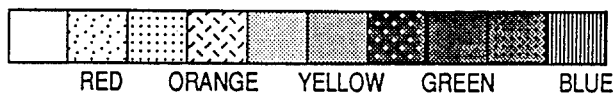
RED  ORANGE  YELLOW  GREEN  BLUE

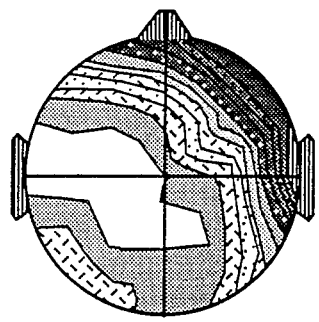
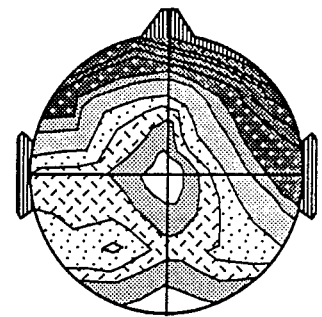
FIG 4A    FIG 4B
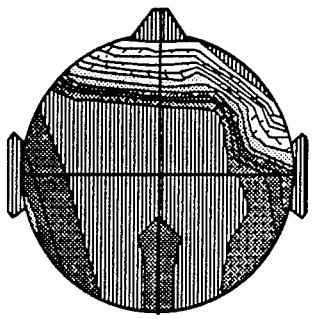
FIG 4C
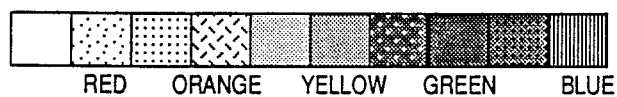
RED  ORANGE  YELLOW  GREEN  BLUE

CROSS CORRELATION ANALYSIS IN BRAIN ELECTRICAL ACTIVITY MAPPING

BACKGROUND OF THE INVENTION

This invention relates to the measurement of brain electrical activity.

Such measurement is based on the localized discrete sampling, both in space and time, of a biological variable. In multichannel evoked potentials (EPs) the underlying biological event is both space and time-variant. To analyze the scalp-recorded activity generated by such events, spatiotemporal relationships must be explicit. This is readily apparent by inspecting the dynamic evolution of topographic maps generated by even simple sensory stimulations. Although topographic maps make biological events more comprehensible, they do not simplify the quantitative evaluation of the phenomenon; on the contrary, new and more complex features are made evident. Expressions such as slowing, lateralized, persistent, focal, and asymmetrical are often used to describe these complex phenomena. Such subjective terminology may be descriptive of the findings but is not easily amenable to a quantitative evaluation. There is a need to quantify these subjective judgments. Doing so will enhance the diagnostic power of event-related potentials Traditional analysis of EP data involees compilation of the latencies to sequential numbers of "standard" positive and negative peaks. This method of analysis has not proven useful for the purposes of topographic mapping for a number of reasons: First, many normal subjects fail to demonstrate the so-called normal peaks and valleys. Second, even for those subjects whose EPs over primary cortex are "classic" in morphology, their EPs at remote locations may appear quite complex and different from the primary response. For example the visual evoked response (Ver) recorded from the anterior temporal electrodes is never a slightly scaled down, latency stretched version of the occipital recorded response, but has its own complex morphology. Third, the presence of pathology may totally distort EP morphology rendering the recognition of standardized components difficult or impossible even over primary cortex.

Brain electrical activity mapping (BEAM) is a known diagnostic tool for detecting brain abnormalities. BEAM is described in U.S. Pat. No. 4,421,122; Duffy et al., "Brain electrical activity mapping (BEAM): A new method for extending the clinical utility of EEG and evoked potential data," Ann. Neurol., 5:309–321 (1979); Duffy, Bartels, et al., "Significance Probability mapping: An aid to the topographic analysis of brain electrical activity," Electroenceph. Clin. Neurophysiol., 512:455–462 (1981); Duffy, *Topographic Mapping of Brain Electrical Activity*, Butterworths (1986) (all incorporated by reference).

SUMMARY OF THE INVENTION

The invention features preparation of three types of cross-correlation maps based on the cross correlation at each of a plurality of electrodes: (1) cross correlation between a patient's EP and the normal EP; (2) the maximum cross-correlation for any time shift in a selected period (preferably 100 msec) (CMax); (3) the time shift at which maximum correlation occurs (TMaxC). In preferred embodiments, the cross-correlation analysis is performed on a selected EP segment; one of four particularly discriminating diagnostic features are computed: (1) the mean of the cross-correlation of each VER EP from each electrode with the normal group VER EP from time 0 to 400 msec with no lagging (CVS1); (2) the left-right difference of the mean of the maximum cross-correlation obtained at any electrode between the subject's and normal group mean auditory evoked response (AER) EP data as lagged across the interval 120–160 msec (CAY1); (3) the maximum value of TMaxC; (4) the minimum value of TMaxC; and a diagnosis is made on the basis of at least two of these diagnostic features.

The new cross correlation analysis (CCA) provides an improved diagnostic tool for detecting and characterizing brain pathology. An advantage of the technique is that the patient's evoked potential cartoon (which previously would have to be viewed on a computer monitor by each physician performing a diagnosis) is reduced to a single image, which can be easily reproduced and transmitted.

Other features and advantages of the invention will be apparent from the following description of preferred embodiments and from the claims.

DESCRIPTION OF THE PREFERRED EMBODIMENT

Drawings

FIGS. 2A–2D are four images generated by cross-correlational analysis.

FIG. 3A is a Z-SPM comparing a subject's AER data to that of a control group.

FIGS. 3B–3E are four images generated by cross-correlational analysis.

FIG. 4A shows the distribution of the correlation coefficient between the AER of a reference population and a subject with a tumor in the right anterior quadrant.

FIG. 4B shows the distribution of MaxC, the maximum value of the correlation coefficient computed for the first 100 msec of the AER of the same subject as FIG. 4A.

FIG. 4C shows the distribution of TMaxC, the latencies where the maximum value of the correlation coefficient was measured in the first 100 msec of the EP. High values of this parameter indicate an increased latency of the EP.

SUMMARY OF METHOD

Figure 1:
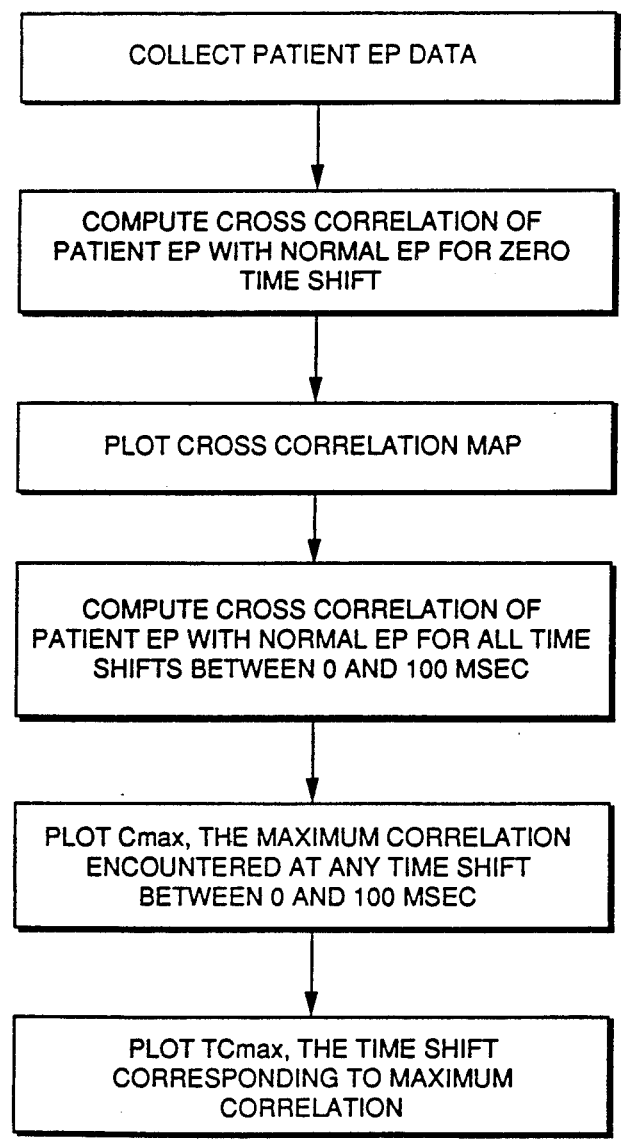
FIG. 1 is a block diagram showing the cross-correlation analysis method of the invention.

Shown in FIG. 1 is a summary of the steps in performing the cross-correlation analysis. The patient's data is gathered, and then compared at all twenty electrodes to a comparable EP for normal patients. If the EP waveforms are identical at any electrode, the result is 100% correlation. Differences in waveform produce lower correlation figures. The correlation figures are displayed as a map (FIG. 4A). Regions of poorest correlation may indicate the presence of a tumor.

A poor correlation between the patient's data and that of the normal group can also be caused by a time shift, or latency, in the patient's EP. To detect such latency, cross-correlation analysis is undertaken for different relative time shifts between the patient's EP and that of the normal group, so-called lagged correlation. It has been found useful to plot the maximum correlation found for any amount of time shift between 0 and 100 msec; this parameter has been called CMax (FIG. 4B). Another useful map is the time in milliseconds corresponding to maximum correlation. This parameter, which we call TMaxC (FIG. 4C), is the time shift required to produce maximum correlation between the patient and the normal group.

These three basic maps—correlation, CMax, and TMaxC—can also be performed on a selected segment of the evoked potential.

SUMMARY OF CLINICAL RESULTS

A first set of feature extraction procedures was aimed at providing a map of the spatial distribution of the EP irrespective of time. This was achieved by means of a cross-correlation analysis (CCA) technique based on the computation of the correlation coefficient between each of the 20 EP waveforms of a given subject and the waveforms of a reference group. These 20 numerical values (the correlation coefficients at time zero, or CCtO) can be used to produce a map. FIG. 4A represents the distribution of the correlation coefficient for a subject with a tumor in the left frontal region. The region of poor similarity is clearly evident. This map represents a measure of difference irrespective of time, and it is impossible to tell if the poor correlation is due to latency or amplitude differences. In order to measure latency shifts, a lagged correlation technique was used and two further features were obtained: the first mapping the maximum value of the correlation obtained within 100 msec lag time (MaxC) and the second showing the time delay to highest correlation (TMaxC). The mapping of MaxC for the same subject shown in FIG. 4A is presented in FIG. 4B. In "pure" delay (i.e., not involving a morphological difference) on one or more channels, the map would have been uniformly distributed. The mapping of TMaxC is presented in FIG. 4C. This last feature is aimed more at quantifying the latency shift, as well as its position on the scalp. In addition to the clinical meaning of each feature, it is important to consider the combined results of different cross-correlation features. For example, a pure latency shift would be indicated by a simultaneous high value of CCA features MaxC and TMaxC, while a low value of MaxC associated with a high value of TMaxC would indicate both a morphological and a latency abnormality of the EP. Other combinations are possible.

Numerical descriptors or features can also be defined using CCA. From the more than 1500 EP features, the most important selected by automated classification techniques include the mean value computed over the electrodes of the CCtO and the minimum and maximum values of the TMaxC. These proved the most powerful in discriminating among normal persons and tumor patients. A combination of these two alone was sufficient to classify correctly 90% of patients. Of these features one was derived from AER, the other from flash VER.

DETAILED DISSUSSION OF CLINICAL RESULTS

Our goal was to explore the ability of evoked potentials to identify the presence or absence of a straightforward clinical lesion, supratentorial brain tumor. We sought to separate the dual issues of tumor detection and tumor localization by addressing them in different analyses. It was our belief that evoked potential ("EP") data are difficult to analyze by unaided visual inspection of multichannel waveforms, each derived from one of many scalp electrodes. Our approach was to first process these data as a series of topographic images using the BEAM method described in U.S. Pat. No. 4,421,122 and Duffy et al., "Brain electrical activity mapping (BEAM): A method for extending the clinical utility of EEG and evoked potential data," *Ann Neurol* 5:309-332, 1979b. Next, we developed two new techniques for extracting numerical measurements of abnormality from these topographic data as described below.

To test the ability of such measurements derived from multichannel EP data to discriminate normal control subjects from those with supratentorial brain tumor, we divided our research population into two equal groups, each, in turn, containing equal numbers of subjects with and without tumors. The first group, designated as the "training set", was used to develop discrimination rules. The second group termed the "test set" was used to determine how well these rules would perform when used prospectively on a data set not used in rule generation. Similar analytic techniques were then used to discriminate between subjects with left or right sided tumors and among subjects with anterior, central, or posterior tumors.

For comparative purposes, the standard EEG records and the unprocessed recordings of EP waveforms for the entire population were read by clinicians using unaided visual inspection, without knowing the subject's identity or diagnosis.

Twenty-two subjects with the diagnosis of supratentorial brain tumor were recruited for our electrophysiological study as paid volunteers. Tumor diagnosis was established on the basis of CT scan, but no subject had as yet received treatment in the form of surgery, radiation, or chemotherapy. Several subjects had received steroids but none were medicated at the time of the study. A few subjects were receiving, or had been receiving, prophylactic anticonvulsant therapy, but none had an active seizure disorder or epileptiform EEG at the time of the study. Of the 22 subjects, 11 had left and 9 had right hemisphere tumors. In two subjects tumor distribution was ambiguous by CT scan so they were dropped from the subsequent localization analysis. For purposes of greater localization, tumors were further categorized as anterior, central-lateral, or posterior. In this topographic classification, the planar projection of the scalp was roughly divided into three equal anterior-posterior parts. All anterior tumors were located in the anterior, middle, or lateral portions of the frontal lobe; central-lateral tumors in the anterior or lateral parietal lobe, posterior frontal lobe, or mid-temporal lobe; and posterior tumors in the posterior parietal, occipital, or posterior temporal regions. Of these 20 subjects, 8 had anterior, 6 lateral, and 6 posterior tumors. Tumor subject's age ranged from 15 to 64 years.

Twenty additional age-matched subjects were recruited and renumerated as controls. Although none of the control population had received CT scans, they were all neurologically normal and were not seeking medical attention at the time of the study. The data from one control subject were lost due to technical error leaving 9 subjects whose data could be analyzed.

The CCA analytic process described below requires comparison to a reference normal population. For this we used control group populations within decade age ranges that were available for clinical comparisons in the laboratory.

Our entire population was studied in the BEAM laboratory of the Seizure Unit at Children's Hospital, Boston. Subjects were seated and tested in a partially reclining chair within a soundproof chamber. Data were recorded from 20 Grass gold cup electrodes applied to the scalp with collodion according to the International 10-20 system of placement (referenced to linked ears). Additional channels were recorded to monitor eye and muscle artifact. Following amplification by a Grass Model 24-D polygraph, EEG data were recorded on a Honeywell 5600E 28 channel tape recorder, along with the appropriate data from trial and event markers, for subsequent off-line analysis. Standard EEG tracings were formed during the eyes open and eyes closed waking state.

During data collection, special care was taken to minimize or eliminate the distorting effects of eye blink, eye movement, and muscle artifact. Eye movements and blinks were monitored on line and a number of maneuvers were used to reduce their frequency. Subjects were made aware of residual eye blinks during eye closure states, were instructed to supress them, and were given frequent pauses ("blink holidays"). During eye open states, subjects were given fixation targets. Time was spent with subjects to achieve relaxation thereby reducing artifact. Recordings were often prolonged to insure sufficient artifact-free periods.

During formation of single averaged EPs, segments containing high voltage artifact, usually attributable to movement or eye blink, were rejected. Rejection level could be individually adjusted, but was usually set at 50 uV. For each electrode site, a single EP was constructed from 256 sampled data points over a 1024 msec interval with the stimulus occurring midway in time. Thus, the first 512 msec formed a baseline (pre-stimulus) epoch. EPs were formed for the following four conditions:

(1) VER: visual evoked response to stroboscopic flash; Grass Model PS-3 at Intensity level 8 placed 30 cm from the subject's closed eyes. A white noise generator masked residual clicks.

(2) BSE: somatosensory evoked response to simultaneous bilateral stimulation of left and right median nerves of each subject just at twitch threshold via a dual channel Grass S8 stimulator (Yamada et al., Somatosensory—evoked potentials elicited by bilateral stimulation of the median nerve and its clinical application, *Neuroloqy* 28:218-223, 1978).

(3) AER: auditory evoked response to a 1000 Hz tone pip 40 msec in length. Sound was generated using a Grason Stadler 1287 electronic switch and transmitted via earphones at 92 db SPL.

(4) PRVER: pattern reversal visual evoked response to a full 256 check field (Grass Model 10 VPG) displayed on a Conrac video monitor placed 64 cm from each subject's open eyes.

For the creation of topographic images single readings were taken from each of the 20 electrodes measuring the actual EP amplitudes at each electrode for each 4 msec post-stimulus latency epoch (Duffy et al., Brain electrical activity mapping (BEAM): A method for extending the clinical utility of EEG and evoked potential data, *Ann Neurol* 5:309-332, 1979b). Scalp areas surrounding the 20 active scalp electrodes were assigned a numerical value by linear interpolation based upon the values at the three nearest electrodes. In this way, values from the 20 original electrodes provide a quantitative basis for a 64×64 matrix of numerical values which were fitted to a color, discrete level, equal interval, intensity scale for display on a color video monitor. Underlying numerical matrices were maintained for subsequent computer analysis.

In this manner standard EEGs, EPs, and topographic maps were prepared for each subject.

Spatial trajectory analysis, as described in my copending application, entitled Spatial Trajectory Analysis in Brain Electrical Activity Mapping, filed on Apr. 13, 1987 (incorporated by reference), was also used in our investigation.

The cross-correlational analysis (CCA) technique was developed to address the difficulties associated with traditional analysis of evoked potential data, and thereby provide additional neurophysiological features from EP data. Initially, the correlation value, "r" is calculated between each of the subject's EPs and the mean EP of the corresponding group mean EPs from a control population. The resulting "r" values based on the 20 electrode readings can then be used to interpolate values for all areas of the brain to form an image, the "r-CCA", where larger values highlight regions of high correlation with the reference population. The 1-r value can be imaged to delineate regions of low correlation, the "(1-r)CCA". Furthermore, lagged correlation (as described below) can then be performed and images made of the maximum correlation achieved ("rmax-CCA") as well as the time to maximum correlation ("t-CCA"). Based on these images, difference attributable to amplitude change can be discriminated from difference attributable to latency shift. FIG. 2 illustrates this process.

Initially an "unknown" EP to be analyzed is considered as a whole with the first 400 msec of this unknown EP correlated with the full 512 msec of the reference group EP, lagging the unknown EP over 100 msec based on the approach of Brazier and Barlow (1956). This yields three features; the maximum correlation achieved, the maximum time delay to highest correlation, and the lowest correlation achieved. Next, the EP epoch is broken down into 11 overlapping time intervals, each of 80 msec duration and beginning 40 msec apart, i.e., 0-80, 40-120, 80-160, etc. For each interval correlation is formed over 40 msec and lagged an additional 40 msec. For each interval the maximum, minimum, and mean correlation and time of maximum correlation are stored as putative features. Finally, the maximum, minimum, and mean values of correlation over all intervals are stored as features. Features descriptive of symmetry are created by separately considering the right and left hemisphere electrodes and subtracting resulting values. All such features are spatially independent and many are also time independent.

The CCA features described above were formed on all subjects and made available for use in various group discriminations. As summarized in our results section, features developed using CCA were used in the present study to discriminate between tumor and non-tumor patients. The power (accuracy) of this discriminatory tool was compared with traditional EEG and EP readings by neurophysiologists.

Automated classification refers to that branch of statistics dealing with formalized development and testing of diagnostic rules. In both our present and previous work, we have used the TICAS software package (Bartels and Weid, "Extraction and evaluation of information from cell images", Proceedings of First Annual Life Science Symposium, Los Alamos, NM, October 1973) to select features for the classification of research subjects. Although developed for image analysis, TI- CAS's capability is independent of the type of data input processed and can be readily used for other applications. We have successfully used the TICAS system to discriminate, on the basis of neurophysiological data.

The first step in automated classification is the development of putative measurements or features designed to be sensitive to the discrimination at hand. In our case, however, many more features are usually available than are needed or can be used. Indeed, automated classification theory dictates an ultimate limit on the number of features per subject that may be used to construct diagnostic rules. If this limit is exceeded, diagnostic rules become to narrowly individualized to training sets and fare poorly when they are ultimately evaluated on sets of test subjects. A statistically sound guide for setting this limit is the division of the number of subjects in the smallest training set group by three. Thus for a training set containing 20 subjects, 10 with condition A and 10 with condition B, no more than 3 or 4 (10/3) features should be used in the final diagnostic rules.

The next step, then, is to reduce the number of putative features on some rational basis so as to comply with the above restriction. In TICAS, feature reduction is begun by eliminating from further consideration those not showing statistically significant outcomes on the Wilcoxon-Mann-Whitney two-sample or U test which determines the ability of each feature, considered singly, to demonstrate group difference. Additonal feature reduction is accomplished by exposing remaining features to an evaluation procedure known as a merit value analysis (MVA). Program FMERIT ranks the "merit" of each feature on the basis of whether the feature can separate individual subjects into two groups. An "intermediate merit value" (IMV) is obtained by the linear combination of two common statistical measures, the "measure of detectability" and an "ambiguity function". Having considered features singly, FMERIT then searches for those of value when considered along with other features of high IMV. This is done by penalizing features that are highly correlated with other chosen features. Therefore, the "final merit value" (FMV) of a given feature is constructed by assessing how unique that feature is, considering its average correlation with other selected features. Features with low FMV (low detectability, high ambiguity, and high average correlation) are discarded.

Then the selected best features are used to develop classification rules on the basis of the "training set" as previously described. There are two general, but differing approaches to this process. The first is a parametric approach. A classic approach to this is described by Cooley and Lohnes Multivariate Data Analysis, Wiley, p. 227, (1971) (TICAS program CLASIF). The CLASIF algoritm is based upon a Bayesian method described by Geisser, S. Posterior odds for multivariate normal classifications, *JR Stat. Soc.* 26:69–76, 1964, for finding the odds that a particular observation belongs to one of any number of multivariate populations. After rule development on a "training set" of up to 10 separate groups, CLASIF computes classification probabilities for individual "test set" subjects and assigns each subject to a criterion group on the basis of his highest probability of group membership relative to the position of group centroids and an estimated common group dispersion matrix. In the present study this approach was used to discriminate tumor subtypes (e.g., left vs. right and anterior vs. lateral vs. posterior).

A second approach to this process is more non-parametric in nature. According to this approach, TICAS uses a program designated DSELECT which relies primarily on rank order discriminations rather than upon Gaussian data distribution. DSELECT is a two group discrimination algorithm which sets up boundaries in multivariate space that are best able to separate the two training subsets with the least chance of error on a purely empirical basis. This results in a series of rules which are sequentially applied to all members of the test set. This approach was used to discriminate between subjects with and without tumor.

When the population available for rule development and testing is limited in number, one may employ a procedure known as "the leaving one man out method" or "jackknifing" (TICAS program JACK and PICK). This technique (Lachenbruch, PA, *Discriminant Analysis*, New York: Hafner Press, 1975) develops diagnostic rules on all subjects except one and then tests the rules on the "left out" subject whose data did not enter the rule development. This subject is then returned to the main group, another subject left out, and the entire rule-making and rule-testing procedure is repeated. The process is reiterated until each subject is left out once. The degree to which left-out subjects are successfully classified gives an indication of how such diagnostic rules, developed on small data sets, might be expected to perform on additional subjects. It is not an ideal procedure, but one of the few available when the number of subjects is limited. Jackknifing was used in this study for the discrimination of tumor subtypes due to the small number of subjects in each tumor subcategory.

1. Tumor vs. No Tumor Study

For this aspect of the research we formed a training set of 21 subjects, 11 with and 10 without tumor. To be conservative we elected to rely upon just two features. Our approach to feature reduction was to initially group them into two broad categories to be considered separately. Certain features were sensitive to abnormality found anywhere in the brain; these we termed global features. Others were primarily sensitive to differences between the hemispheres; these we termed "symmetry features". As tumors may produce both global and regional change, our empirical decision was to choose the best global feature and the best symmetry feature as the final two features for creating decision rules. Accordingly, global and symmetry features were separately analyzed by MVA (see previous discussion) for each of the four EP modalities used. The top 5 features of each type by FMV from each EP data set were placed into two corresponding groups of 20 and MVA repeated on each group separately. The best global feature by FMV was CSV1 and the best symmetry feature CAY1 (See Table 1A). Training set classification rules were created by DSELECT and when reapplied to the training set were 100% successful. Next the rule was then applied to a 20 member test set containing 11 subjects with and 9 without tumor. Overall classification success was 90% (18 of 20) with only one subject in each category misclassified. Results are summarized in Table 2A.

Two clinical electroencephalographers independently and blindly evaluated the standard 24 channel paper records and on this basis classified subjects as tumor or non-tumor. Each reader correctly classified 76% of the records. Most of the false positives were shared, but only half the false negatives were shared between the two readers (see Table 2A).

These neurophysiologists independently and blindly evaluated the 80 EP waveforms (4 sets of 20) from each and on the basis of component latency, amplitude and morphology classified subjects as tumor or non-tumor. Success rate varied from 61% to 68%, averaging 64% for all subjects. There were as many false positive as false negative results. Less than half the misclassifications were in common to all readers (see Table 2A).

2. Left Sided vs. Right Sided Tumor Study

Given the small size of our population (11 left-sided tumors and 9 right), we chose the jackknifing technique for this discrimination. As previously described the same training set/test set approach was used; the process was repeated 20 times, each time with differing training sets of 19 and test set of 1. For each analysis, feature reduction was separately performed on the basis of the training set data structure. Although their rank order frequently differed, the same four features were consistently selected by FMV in each case, these being AET1, AET4, BST2, BST3 (see Table 1B). Classification rules were made with program CLASIF, since this conservative algorithm is apt to be less sensitive to noise within small data sets. Our results using these four STA-selected features and CLASIF were very positive. Overall lateral classification success of the "left out" subjects was 95% (19 of 20). All left sided tumors were correctly identified and only one right sided tumor was misclassified. These results are summarized in Table 2B.

3. Anterior vs. Central-Lateral vs. Posterior ttudy

Of our 20 subjects with brain tumor, the lesion was anterior in 8, central-lateral in 6, and posterior in 6. Once again, because of the small size of the individual data subsets, we elected to employ the jackknifing technique with the CLASIF model. For such a three group classification problem, three times the number of features suggested by Foley may be used, i.e., (6/3) * 3 = 6. For each training set, a three way comparison was performed and the best two features from each comparison were used to generate rules. As with the lateralization analysis, a consistent set of features were indicated by FMV in all but 2 cases, these being, TAE1, TAE2, TAE3, TAE4, TBS1, TBS2 (see Table 1C). Accordingly, we chose to generate rules using these 6 in every case. Overall classification success of the "left-out" subjects was 80% (16 of 20). Five of the 8 anterior, 6 of the 6 central-lateral, and 5 of the 6 posterior were correctly identified. These results are summarized in Table 2C.

TABLE 1

DESCRIPTION OF CCA AND STA SELECTED FEATURES

A. TUMOR VS NON-TUMOR STUDY

| | | |
|---|---|---|
| *CSV1 (VER,CCA) | | Mean of the cross-correlation of each EP from each electrode with the corresponding control group EP from time 0 to 400 msec with no lagging. |
| *CAY1 (AER,CCA) | | The left-right difference of the mean of the maximum cross-correlation obtained at any electrode between the subject's and control group mean EP data as lagged across the interval 120-16- msec. |

B. LEFT VS RIGHT SIDED TUMOR STUDY

| | |
|---|---|
| *AET1 (AER,STA) | Th X position of the COG, mean value in the interval 400-440 msec. |

TABLE 1-continued

DESCRIPTION OF CCA AND STA SELECTED FEATURES

| | |
|---|---|
| AET2 (AER,STA) | Minimum of the maximum amplitude per frame in the 400-440 msec interval. |
| BST2 (BSE,STA) | Minimum area above threshold in the 200-240 msec interval. |
| *BST3 (BSE,STA) | Maximum X value of the boundary of the area above threshold in the 440-480 msec interval. |

C. ANTERIOR VS CENTRAL-LATERL VS POSTERIOR TUMOR STUDY

| | |
|---|---|
| TAE1 (AER,STA) | Minimum of the maximum amplitude per frame for the 240-280 msec interval. |
| TAE2 (AER,STA) | Minimum of the maximum amplitude per frame for the 440-480 msec interval. |
| *TAE3 (AER STA) | Maximum X value of the boundary of the area above threshold in the 200-240 msec interval. |
| *TAE4 (AER,STA) | Mean change of the X position of the COG of the 200-240 msec interval. |
| *TBS1 (BSE,STA) | Maximum Y value of the boundary of the area above threshold in the 272-368 msec interval. |
| *TBS2 (BSE,STA) | Mean change of Y position of the COG in the 200-240 msec interval. |

*Most discriminatng features

TABLE 2

RESULT SUMMARY: RATIOS OF CORRECT CLASSIFICATIONS TO TOTAL SUBJECTS DIAGNOSED

A. TUMOR VS NON-TUMOR STUDY

1. Visual Inspection of EEG by Neurophysiologists

| | CONTROL | TUMOR | OVERALL |
|---|---|---|---|
| Reader A | 15/19 | 16/22 | 31/41 (76%) |
| Reader B | 14/19 | 17/22 | 31/41 (76%) |
| Shared Errors A:B | 4 | 3 | AVG: (76%) |

2. Visual Inspection of EP Waveforms by Neurophysiologists

| | | | |
|---|---|---|---|
| Reader A | 11/19 | 14/22 | 25/41 (61%) |
| Reader B | 15/19 | 11/22 | 26/41 (63%) |
| Reader C | 13/19 | 15/22 | 28/41 (68%) |
| Shared Errors | | | |
| A:B | 2 | 4 | AVG: (64%) |
| A:C | 3 | 6 | |
| B:6 | 3 | 3 | |

3. Automated Classification (Features CSV1, CAY1)

| | | | |
|---|---|---|---|
| Training Set | 10/10 | 11/11 | 21/21 (100%) |
| Test Set | 8/9 | 10/11 | 12/20 (90%) |

B. LEFT VS RIGHT SIDED TUMOR (Features AET1, AET4, BST2, BST3)

| | LEFT | RIGHT | OVERALL |
|---|---|---|---|
| Jackknifing | 11/11 | 8/9 | 19/20 (95%) |

C. ANTERIOR VS CENTRAL-LATERAL VS POSTERIOR TUMOR (Features TAE1, TAE2, TAE3, TAE4, TBS1, TBS2)

| ANTERIOR | CENTRAL LATERAL | POSTERIOR | OVERALL |
|---|---|---|---|
| Jackknifing 5/8 | 6/6 | 5/6 | 16/20 (80%) |

The basic intent of this investigation was to evaluate whether long latency EP data contain clinically valuable information. The observation that such EPs are not routinely employed to investigate subjects with suspected hemispheric dysfunction suggested to us that any information they might contain must be difficult to extrapolate. Indeed, in our study, three neurophysiologists were barely above the "chance" level of success (64%) in discriminating, by unaided visual inspection of multi-channel, multi-modality EPs between subjects with and without brain tumor. It was retrospectively agreed that the variation induced by presence of tumor remained largely hidden within apparently normal subject-to-subject variability and could only be clearly identified under the condition that the underlying mass lesion was particularly large and/or correspondingly destructive. The specific task, therefore, was to see if a more quantitative approach might improve success in this discrimination.

Accordingly, initial efforts were devoted to developing, from a given subject's EP data, new numerical features to be used in such a quantified analysis. Observations made during the daily clinical evaluation of EP data, especially those topographically mapped, were utilized. Small or early lesions were noted to prolong the latency of (elongate) EPs. Large or later lesions were even more destructive of expected EP waveform morphology. Such changes could be either regional (usually small or early lesions) or generalized (usually larger or late lesions). The CCA technique was developed to take advantage of these clinical observations. This cross-correlation measure is sensitive to changes in both EP morphology and latency. As demonstrated in FIG. 2, tumors tend to show poor regional correlation with control group data. EP data on tumor patients exhibit prolonged delays to maximum correlation when a lagged correlation is performed. A further observation was made that in normal subjects the topographic distribution (positive and negative maxima—peaks and troughs) of EP data changes over time in a non-random manner often showing midline anterior-posterior or symmetrical medial-lateral movement of maxima. Such peak movement has been documented by Sandini et al., "Topography of brain electrical activity: A bioengineering approach," *Med Prog. through Technology* 10:5-19 (1983) who used this medial-lateral motion for functional localization using VER data. Pathology, however, greatly alters this spatio-temporal pattern and induces major distortion of peak trajectories. We commonly observe that peaks appear late overlying tumors, eventually becoming above-average in amplitude, and exhibiting prolonged duration (Duffy et al., Brain electrical activity mapping (BEAM): A method for extending the clinical utility of EEG and evoked potential data, *Ann Neurol* 5:309-332, 1979b; Duffy, F. H., Topographic display of evoked potentials: Clinical applications of brain electrical activity mapping (BEAM). *Ann N.Y. Acad. Sci.* 388:183-196, 1982).

Using two features derived from CCA, the automated classification process resulted in the correct prospective classification of 90% of subjects with and without brain tumor. This successful discrimination confirmed our belief that long latency EP data do indeed contain clinically useful information. It also supported the view that such analyses are more difficult to perform by simple unaided visual inspection; only 64% of the test subjects were correctly classified by neurophysiologist inspection of the underlying EP waveforms. The use of CCA and STA appears to provide a significant improvement in EP analysis.

Of note was the low percentage of correctly identified tumors by visual inspection of EEG (Table 2A). It is well known that, in the absence of edema, the charateristic focal slowing associated with tumors may not be detected or, if once present, may vanish following intravenous urea or steroids. Most of our subjects showed little edema on their CT scans. More surprising was the false positive readings of normal subjects' records by our neurophysiologists. As most of the false positive classifications were shared by the two EEG readers, it is probable that minor and presumably normal variations in EEG symmetry were over-interpreted. This underscores the necessity of including normal subjects in such studies and the performance of EEG readings on a blind basis.

Although tumor detection by automated classification of EP was superior to that by visual inspection of EEG, we do not suggest that EP data are inherently more valuable than EEG data. The EEG results are simply presented as a benchmark for comparative purposes in establishing that EP data, when properly analyzed, are clinically applicable.

Using the jackknifing technique and features derived from STA, success in prospective lateral classification of left and right hemispheric tumors was 5%, as seen in Table 2B. Localizations to one of three brain regions was 80% correct overall, although the localization criteria used proved to be much better for central-lateral (100%) and posterior (83%) regions than for the anterior (63%) region (Table 2C). We speculate that residual eye movement/blink artifact may have diminished the sensitivity of frontal lobe features in our identification. These results are in line with Van de Drift's, *The Significance of Electroencephalography for the Diagnosis and Localization of Cerebral Tumors; Leiden; Stenfert Kroese*, (1957), study of tumor localization by EEG except for a higher correct EEG localization of frontal tumors (89%). The distinction between eye artifact and real brain frontal electrical activity may be clearer for EEG than for EP data.

Nonetheless, by automated classification, our tumor localization from long latency EP data was surprisingly good, well beyond the pessimistic result recently summarized by Chiappa, *Evoked Potentials in Clinical Medicine*, New York: Raven Press (1983). To some degree this may reflect the fact that many authors, when studying cerebral lesions, have limited themselves to the PRVER derived from a small number of electrodes. In our data set, the PRVER failed to contribute any features to our final analyses. We feel this results from the relatively restricted topographic distribution of the PRVER, largely limited to posterior quadrants. In contrast, the VER, AER, and BSER modalities evoked widespread changes over all cortex at some point in their EP epoch.

Although it has been most clearly documented that false localization can result from the use of PRVER data (Blumhardt, et al., *The Pattern-evoked Potential in Lesions of the Posterior Visual Pathways*, Ann N.Y. Acad Sci 388: 264-289 (1982), Hoeppner, et al., *Visual Evoked Potentials after Partial Occipital Lobectomy*, Electroenceph Clin Neurophysiol 50:184 (1980), it was not limited to this modality in our data. Whereas the vast majority of features useful in detecting the presence or absence of tumors fell between 100 and 200 msec latency (e.g. CAY1), features in this latency range were much less useful for tumor localization. All features useful in localization were derived from measurements taken after 200 msec and many after 400 msec. Inspection of the topographic data underlying the "detecting" 100-200 msec features often revealed a small potential hill of one polarity over the tumor with a larger area of the opposite polarity surrounding the lesion, even extending into the other hemisphere. This configuration suggested a dipole radially oriented from the center of the lesion but with the distal end of the dipole nearest the scalp (Wood, *Application of Dipole Localization Methods to Source Identification of Human Evoked Potentials*, Ann N.Y. Acad Sci 388: 139-155 (1982)). This emphasizes that EP scalp topography is influenced not only by the location and magnitude of a dipole source, but also by its local orientation. The latter appears to be the most important factor explaining false EP localization (Blumhardt and Halliday, *Hemispheric Contributions to the Composition of the Pattern Evoked Potential Waveform*, Exp Brain Res 36:53-69 (1979)). Of clinical importance, however, is the observation that features providing reliable localizing information can be derived from later EP components, at a point greater than 200 msec in the EP.

Multimodal and multielectrode long latency evoked potential data were analyzed for subjects with and without CT scan verified, but otherwise untreated supratentorial brain tumor. Using topographic displays to compare the tumor subjects to normals, it was found that tumors exhibit poor regional correlation with control group data and prolonged regional delays to maximum correlation when EP recordings are lagged in time. In addition, Spatial Trajectory Analysis (STA) was used to demonstrate brain tumor induced distortions in the velocity, amplitude and trajectory of the topographic peaks and troughs of EP activity which move across the scalp with time.

Using two numerical features derived from CCA, automated classification procedures were applied to a "training set" of subjects with and without brain tumor and the resulting diagnostic rules were 90% correct in the classification of similar subjects in a separate "test set". This compared well to a 64% correct classification by diagnosticians using unaided visual inspection of EP waveforms and 76% correct classification by similar inspection of EEG records.

Based upon numerical features derived from STA, prospective classification success in tumor localization by the "leaving one man out method" was 95% for left versus right sided tumors and 80% correct for localization of tumors to the anterior, middle or posterior third of the head.

Thus, long latency EP data contain information useful in the recognition and localization of hemispheric lesions.

In FIG. 2 there are shown four BEAM images, each representing the output of the procedure for the AER of a subject with an untreated right hemispheric brain tumor located in the lateral portion of the frontal loe. FIG. 2A illustrates the cross correlation between the patient's data and the age appropriate control group. Positive correlations are shown in red-orange, and negative in blue. The correlations at time $=0$ (no lag) are shown. The maximum correlation (Rmax) was 0.80, peaking in the left central region. Of more interest, the minimum correlation (Rmin) was extremely low ($-0.72$) and located in the right mid to anterior temporal region near the tumor site. FIG. 2B shows the maximum correlation achieved when the subject's EP data were lagged over a 100 msec window. A different scale convention was employed. Rmax was $+0.92$, again over the left hemisphere and Rmin ($-0.29$) was located over the tumor site. FIG. 2C illustrates lag time to achieve maximum correlation. The greatest time lag necessary to achieve maximum correlation was 96 msec after EP onset and was topographically localized to the tumor site. FIG. 2D shows the inverse correlation data (1-R) of FIG. 2B above. Redisplaying such data in this manner serves to highlight regions of poor correlation. Note the similarity between FIG. 2C and FIG. 2D indicating that poorest correlation and greatest latency shift are topographically coincident. Such images demonstrate how poor correlation (FIGS. 2A, 2B, 2D) and length of time to maximum correlation (FIG. 2C) can delineate focal lesions.

Further images are shown in FIGS. 3A-3E to demonstrate the CCA method. FIG. 3A is the Z-SPM resulting from the direct comparison of the subject's AER data in the 280-356 msec epoch to an age appropriate control group. The unoperated right lateral frontal brain tumor is well demarcated, the maximum z value is 3.31.

The images of FIGS. 3B613 3E are derived by the CCA method. FIG. 3B illustrates the cross correlation between the patient's data and the age appropriate control group. The maximum correlation (Rmax) was 0.80 peaking in the left central region. Of more interest, the minimum correlation (Rmin) was extremely low, $-0.02$ and located in the right mid to anterior temporal region (near the tumor site). FIG. 3C shows the maximum correlation achieved at all possible time lags. Rmax was $+0.89$, again over the left hemisphere and Rmin was over the tumor site. Just below in FIG. 3E, the (1-R) of FIG. 3C data is shown. Here, the poor correlation shown by higher color scales locates the lesion.

FIG. 3D illustrates lag time to achieve maximum correlation. Rmax, as shown in FIG. 3C was achieved 98 msec after EP onset.

FIGS. 3B to 3E demonstrate how poor correlation (B, C, E) and length of time to maximum correlation (D) can delineate focal lesions such as that delineated by the older Z-SPM method in FIG. 3A.

Other embodiments are within the following claims.

What is claimed is:

1. The method of detecting and characterizing brain pathology in patient, comprising the steps of:
    gathering the patient's evoked potential for a plurality of electrodes;
    for each electrode performing a cross-correlation of the patient's evoked potential to an evoked potential for a respective electrode of a normal patient to obtain a plurality of cross-correlation figures;
    mapping the cross-correlation figures for each electrode; and
    using said mapped cross-correlation figures to detect and characterize brain pathology.

2. The method of claim 1 wherein said cross-correlation is performed for a selected segment of the evoked potential.

3. The method of claim 1 wherein said step of gathering comprises gathering a patient's visual evoked response evoked potential for each said electrode and wherein said step of performing comprises computing a numerical diagnostic feature comprising the mean of the cross-correlation of each said visual evoked response evoked potential from each electrode with a normal visual evoked response evoked potential from time 0 to 400 msec with no lagging between the patient's evoked potential and the normal evoked potential (CVS1).

4. The method of detecting and characterizing brain pathology in a patient, comprising the steps of:
- gathering the patient's evoked potential for a plurality of electrodes;
- for each electrode performing a cross-correlation of the patient's evoked potential to an evoked potential for a respective electrode of a normal patient for selected relative time shifts between the patient's evoked potential and the normal evoked potential to obtain a plurality of cross-correlation figures for each electrode;
- selecting, for each electrode, the maximum cross-correlation figure;
- mapping the selected maximum cross-correlation figures; and
- using said mapped cross-correlation figures to detect and characterize brain pathology.

5. The method of claim 4 wherein said selected time shifts span the range from 0 to 100 msec.

6. The method of claim 3 further comprising computing a numerical diagnostic feature comprising the maximum value of said selected cross-correlation figures.

7. The method of claim 5 further comprising computing a numerical diagnostic feature comprising the minimum value of said selected cross-correlation figures.

8. The method of claim 4 wherein said step of gathering comprises gathering a patient's visual evoked response evoked potential for each said electrode and wherein said step of performing comprises computing a first numerical diagnostic feature comprising the mean of the cross-correlation of each said visual evoked response evoked potential from each electrode with a normal visual evoked response evoked potential from time 0 to 400 msec with no lagging between the patient's evoked potential and the normal evoked potential, (CVS1),
wherein said method further comprises computing a second numerical diagnostic feature comprising the maximum value of said selected cross-correlation figures,
wherein said method further comprises computing a third numerical diagnostic feature comprising the minimum value of said selected cross-correlation figures, and
wherein a diagnosis is made on the basis of two of said numerical diagnostic features.

9. The method of claim 4 wherein said cross-correlation is performed for a selected segment of the evoked potential.

10. The method of claim 4 wherein said step of gathering comprises gathering a patient's auditory evoked response evoked potential for each said electrode and wherein said step of performing comprises computing a numerical diagnostic feature comprising the left-right difference of the mean of the maximum cross-correlation obtained at any electrode between the patient's auditory evoked response evoked potential and a normal mean auditory evoked response evoked potential for various time shifts between the patient's evoked potential and the normal evoked potential across the interval 120–160 msec (CAY1).

11. The method of detecting and characterizing brain pathology in a patient, comprising the steps of:
- gathering the patient's evoked potential for a plurality of electrodes;
- for each electrode performing a corss-correlation of the patient's evoked potential to an evoked potential for a respective electrode of a normal patient for selected relative time shifts between the patient's evoked potential and the normal evoked potential;
- mapping the time shift at which maximum cross-correlation occurred (TMaxC) for each electrode; and
- using said mapped time shifts to detect and characterize brain pathology.

12. The method of claim 11 wherein said selected time shifts span the range from 0 to 100 msec.

13. The method of claim 11 wherein said cross-correlation is performed for a selected segment of the evoked potential.

* * * * *

UNITED STATES PATENT AND TRADEMARK OFFICE
CERTIFICATE OF CORRECTION

PATENT NO. : 4,844,086

DATED : July 4, 1989

INVENTOR(S) : Duffy

It is certified that error appears in the above-identified patent and that said Letters Patent is hereby corrected as shown below:

Title page:

Abstract, line 9, "one" should be --ones--.

Col. 1, line 27, insert --.-- after "potentials".
Col. 1, line 28, "involees" should be --involves--.
Col. 1, line 37, insert --,-- after "example".
Col. 1, line 38, "Ver" should be --VER--.
Col. 2, line 31, "correlational" should be --correlation--.
Col. 2, line 35, "correlational" should be --correlation--.
Col. 5, lines 45-46, "Neuroloqy" should be --Neurology--.
Col. 6, line 10, "cross-correlational" should be --cross-correlation--.
Col. 9, line 29, "ttudy" should be --Study--.
Col. 12, line 27, "5%" should be --95%--.
Col. 13, line 28, insert --CCA-- after "of".
Col. 13, line 57, insert --CCA-- before "procedure".
Col. 13, line 59, "loe" should be --lobe--.
Col. 14, line 25, "3B613 3E" should be --3B-3E--.
Col. 14, line 48, insert --a-- before "patient".
Col. 15, line 23, "3" should be "5"
Col. 15, line 41, delete "," after "potential".
Col. 16, line 28, "corss" should be --cross--.

Signed and Sealed this

Twelfth Day of June, 1990

Attest:

HARRY F. MANBECK, JR.

*Attesting Officer*      *Commissioner of Patents and Trademarks*